(12) United States Patent
Biegelsen

(10) Patent No.: US 7,235,123 B1
(45) Date of Patent: Jun. 26, 2007

(54) PARTICLE TRANSPORT AND NEAR FIELD ANALYTICAL DETECTION

(75) Inventor: David Biegelsen, Portola Valley, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 295 days.

(21) Appl. No.: 10/977,834

(22) Filed: Oct. 29, 2004

(51) Int. Cl.
 *B03C 3/34* (2006.01)
 *B03C 3/47* (2006.01)

(52) U.S. Cl. .................. 96/26; 96/66; 96/98; 96/413; 96/418; 204/556; 204/665; 204/674; 210/93; 210/243; 210/748

(58) Field of Classification Search ............ 96/413, 96/418, 26, 65, 66, 98; 210/93, 243, 748; 204/556, 665, 674
See application file for complete search history.

(56) References Cited

U.S. PATENT DOCUMENTS

| | | | | |
|---|---|---|---|---|
| 1,605,648 A * | 11/1926 | Cooke | ........................ | 95/79 |
| 3,431,411 A * | 3/1969 | Harrick | ................ | 250/339.12 |
| 3,718,029 A * | 2/1973 | Gourdine et al. | .......... | 73/28.02 |
| 3,755,122 A * | 8/1973 | Melcher et al. | ............. | 204/554 |
| 3,879,986 A * | 4/1975 | Sehmel | ....................... | 73/28.04 |
| 4,038,049 A * | 7/1977 | Melcher et al. | ................ | 95/62 |
| 4,376,637 A * | 3/1983 | Yang | ............................. | 95/74 |
| 4,472,278 A * | 9/1984 | Suzuki | ....................... | 210/243 |
| 4,527,884 A | 7/1985 | Nusser | ....................... | 399/266 |
| 4,558,941 A | 12/1985 | Nosaki et al. | ............. | 399/266 |
| 4,647,179 A | 3/1987 | Schmidlin | ................... | 399/285 |
| 4,896,174 A | 1/1990 | Stearns | ....................... | 347/120 |
| 5,281,982 A | 1/1994 | Mosehauer et al. | ........... | 347/55 |
| 5,400,062 A | 3/1995 | Salmon | ....................... | 347/55 |
| 5,679,137 A * | 10/1997 | Erdman et al. | ................ | 96/26 |
| 5,717,986 A | 2/1998 | Vo et al. | ..................... | 399/291 |
| 5,850,587 A | 12/1998 | Schmidlin | ................... | 399/258 |
| 5,893,015 A | 4/1999 | Mojarradi et al. | .......... | 399/291 |
| 6,070,036 A | 5/2000 | Thompson et al. | ......... | 399/266 |
| 6,077,334 A * | 6/2000 | Joannou | ....................... | 96/66 |
| 6,112,044 A | 8/2000 | Thompson et al. | ......... | 399/285 |
| 6,134,412 A | 10/2000 | Thompson | .................. | 399/266 |
| 6,137,979 A | 10/2000 | Gartstein et al. | ........... | 399/266 |
| 6,219,515 B1 | 4/2001 | Lestrange | .................... | 399/289 |
| 6,246,855 B1 | 6/2001 | Gartstein et al. | ........... | 399/281 |
| 6,272,296 B1 | 8/2001 | Gartstein | ..................... | 399/55 |
| 6,290,342 B1 | 9/2001 | Vo et al. | ........................ | 347/85 |
| 6,351,623 B1 | 2/2002 | Thayer et al. | ............... | 399/258 |
| 6,499,831 B2 | 12/2002 | Schmidlin | .................... | 347/55 |
| 6,773,489 B2 * | 8/2004 | Dunn | ............................ | 95/78 |
| 6,807,874 B2 * | 10/2004 | Totoki | ..................... | 73/864.71 |
| 6,881,246 B2 * | 4/2005 | Totoki | ............................ | 96/26 |
| 6,899,748 B2 * | 5/2005 | Mohamed | ........................ | 96/3 |
| 6,923,848 B2 * | 8/2005 | Totoki | ............................ | 96/26 |
| 7,090,718 B2 * | 8/2006 | Nybom | ............................ | 96/94 |
| 7,156,970 B2 * | 1/2007 | Lean et al. | .................. | 204/547 |

(Continued)

FOREIGN PATENT DOCUMENTS

EP      0 372 750 A1 *    6/1990      ................... 96/26

*Primary Examiner*—Richard L. Chiesa
(74) *Attorney, Agent, or Firm*—Faye Sharpe LLP

(57) ABSTRACT

Particle collection, transport, and detection systems are disclosed. The systems are uniquely adapted for collecting or concentrating particles from a flowing medium and then transporting the collected particles to a desired location or for subsequent analysis. Electrostatic traveling wave grids can be used in conjunction with sample concentrators.

16 Claims, 6 Drawing Sheets

U.S. PATENT DOCUMENTS

| | | | |
|---|---|---|---|
| 2003/0136205 A1* | 7/2003 | Totoki | 73/864.71 |
| 2004/0251135 A1* | 12/2004 | Lean et al. | 204/456 |
| 2004/0251139 A1* | 12/2004 | Lean et al. | 204/606 |
| 2005/0123992 A1* | 6/2005 | Volkel et al. | 435/7.1 |
| 2005/0247564 A1* | 11/2005 | Volkel et al. | 204/600 |
| 2005/0247565 A1* | 11/2005 | Hsieh et al. | 204/600 |
| 2006/0121555 A1* | 6/2006 | Lean et al. | 435/30 |

* cited by examiner

PARTICLE TRANSPORT AND NEAR FIELD ANALYTICAL DETECTION

BACKGROUND

The present exemplary embodiment relates to the detection and transport of small particles. It finds particular application in conjunction with the scientific instrumentation arts, and will be described with particular reference thereto. However, it is to be appreciated that the present exemplary embodiment is also amenable to other like applications.

In many analytical and instrumentation environments it is necessary to detect or obtain measurements of particles that are dispersed throughout a liquid or gas medium. This can be very difficult if not impossible if the particles are at relatively low concentration levels in the medium. This phenomenon can also occur when attempting to detect or measure liquid droplets dispersed throughout a gas medium. Accordingly, there is a need for a system and method to enable or at least improve the detection or measurement of particles or droplets of liquid in a medium.

It is known to utilize a tapered duct or narrowed flow channel to promote detection or measurement of particles in a flowing stream. However, a mere tapering or constriction in the flow channel is undesirable in that such geometry results in an increased flow impedance. In addition, such tapering or other geometry change does not change the relative concentrations of particles in the flow stream.

Particles can be manipulated by subjecting them to traveling electric fields. Such traveling fields are produced by applying appropriate voltages to microelectrode arrays of suitable design. Traveling electric fields are generated by applying voltages of suitable frequency and phases to the electrodes.

Although a wide array of particle transport systems are known, including those that use traveling electric fields, a need remains for strategies and systems that are particularly adapted for selectively transporting particles over certain paths, or in a certain manner; systems that can be readily implemented and used with currently available instrumentation; and systems of relatively small size that can be used to selectively transport and/or mix multiple populations of particles. Specifically, a need remains for improved transport systems that can be readily utilized in conjunction with analytical instruments.

BRIEF DESCRIPTION

In accordance with one aspect of the present exemplary embodiment, a system for collecting particles and transporting the collected particles is provided. The system comprises a source of sample dispersed in a gas or liquid medium. The system also comprises a sample concentrator in communication with the source and adapted to collect the sample. The system further comprises a traveling wave grid extending from a first location at which the concentrator is located to a second location. Upon operation of the concentrator and the traveling wave grid, the sample is collected from the medium and transported to the second location.

In accordance with yet another aspect of the present exemplary embodiment, a system for collecting particles from a medium and subjecting the collected particles to an analytical operation is provided. The system comprises a source of sample dispersed in a medium. The system also comprises a concentrator in communication with the source. The system further comprises a device adapted to perform a detection and/or analytical operation. And, the system comprises a traveling wave grid extending between the concentrator and the device and adapted to transport collected sample to the device.

In accordance with another aspect of the present exemplary embodiment, a system for collecting particles and transporting the collected particles from a flowing stream of particles in a medium is provided. The system comprises a member adapted to receive and house a flow stream of a medium and particles dispersed therein. The system also comprises a filter body disposed at least partially within the flow stream. The filter body defines a face directed to the approaching flow stream. The filter body is adapted to collect particles from the flow stream. The system also comprises a traveling wave grid disposed proximate to the face of the filter body. Upon operation of the traveling wave grid, particles collected by the filter body are transported from a first region of the grid to the second region of the grid.

DETAILED DESCRIPTION

Figure 1:
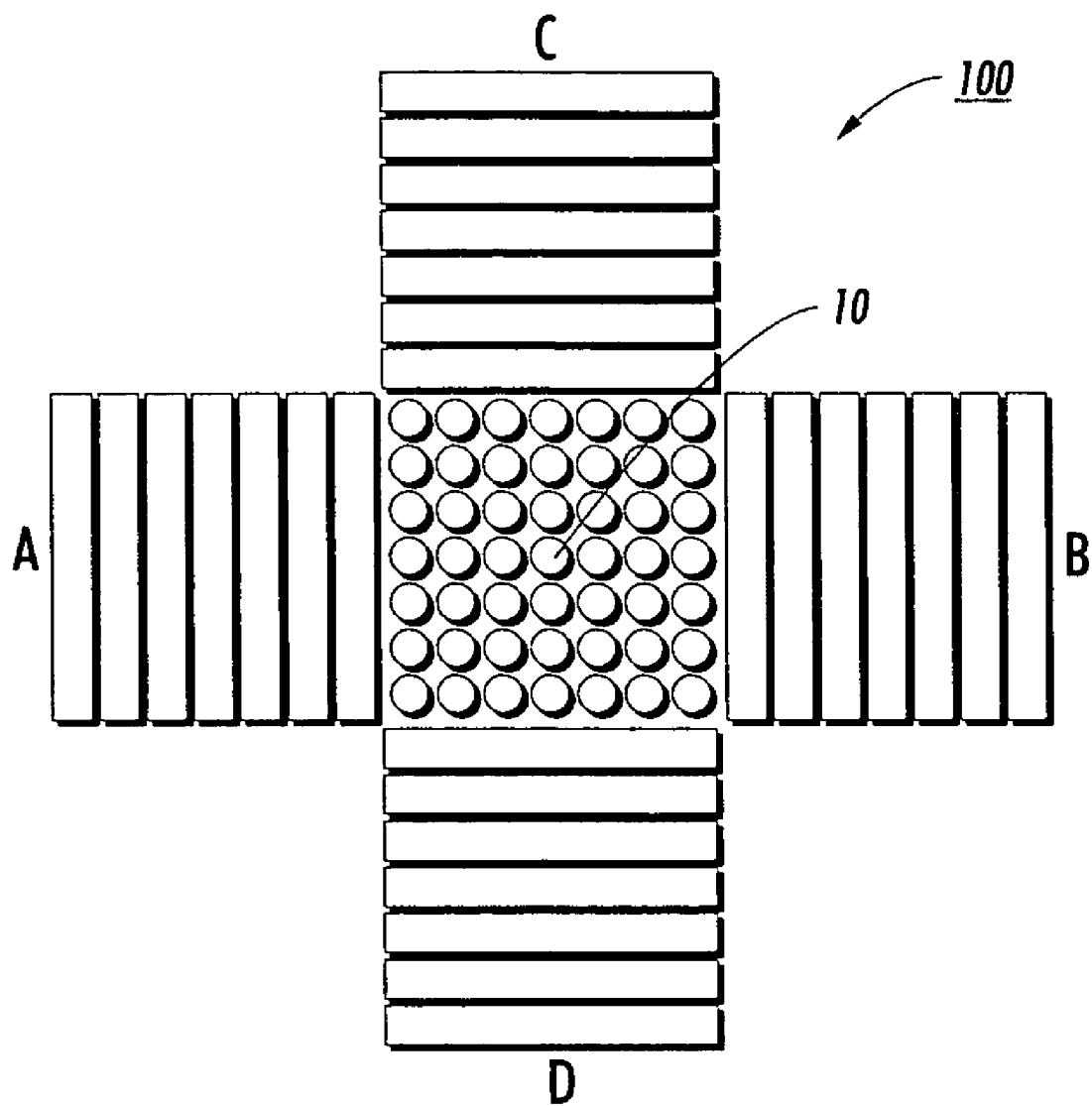
FIG. 1 is a schematic illustration of an exemplary embodiment system for transporting particles.

The exemplary embodiment provides strategies and systems for transporting particles, and specifically for selectively directing them to a specific location, such as for example to an analytical device for detecting or otherwise analyzing the particles. Although many of the exemplary embodiments are described in terms of the instrumentation arts, it is to be understood that the exemplary embodiments include other applications involving the storage, transport, or distribution of minute particles, such as for example in the handling of pharmaceutical powders. As described and illustrated herein, many of the exemplary embodiments utilize an electrode pattern that is provided and configured in such a way that in-plane traveling electrostatic fields can be created and controlled. With each electrode separately addressable, the phases and amplitudes of the signals to the electrodes can be used to synthetically approximate any pattern below the Nyquist limit. Generally, the collection of electrodes used in the exemplary embodiment system and methods are in the form of a traveling wave grid.

In one embodiment, a system and related method are provided for collecting particles from a liquid or gas, and transporting them to a desired location. In yet another embodiment, a system and related method are provided for collecting particles from a liquid or gas and then subjecting the particles to one or more analytical or detection operations. In yet a further embodiment, a system and related method are provided for collecting particles from a liquid or gas, transporting the collected particles, and subjecting the particles to an analytical operation. These aspects are all described in greater detail herein.

In many of the systems and methods described herein, the term sample is used. "Sample" generally refers to any small particle or droplet which is contained in a larger volume of a second material, generally a medium. The sample can be a solid particulate or a liquid. The medium can be either gaseous or liquid, and can be either flowing or generally static. Examples of sample systems include, but are not limited to, particulates dispersed in a gaseous medium; particulates dispersed in a liquid medium; liquid droplets dispersed in a gaseous medium such as an aerosol; and liquid droplets dispersed in a second liquid medium.

The term traveling wave grid as used herein collectively refers to a substrate, a plurality of electrodes to which a voltage waveform is applied to generate the traveling wave(s), or wave packets (localized waves which are limited in spatial extent), and one or more busses, vias, and electrical contact pads to distribute the electrical signals (or voltage potentials) throughout the grid. The term also collectively refers to one or more sources of electrical power, which provides the multi-phase electrical signal for operating the grid. The traveling wave grids may be in nearly any form, such as for example a flat planar form, or a non-planar form. Traveling wave grids, their use, and manufacture are generally described in U.S. Pat. Nos. 6,351,623; 6,290,342; 6,272,296; 6,246,855; 6,219,515; 6,137,979; 6,134,412; 5,893,015; and 4,896,174, all of which are hereby incorporated by reference.

In the various exemplary embodiments of traveling wave grid assemblies described herein, the assembly generally comprises a substrate and a collection of traveling wave electrodes disposed or otherwise deposited or formed on the substrate. In many of the exemplary embodiments, the traveling wave grid is in the form of a multi-leg pattern. That is, the assembly includes at least a first leg, a second leg, and a third leg in which the legs are generally in electrical communication with each other, and in most embodiments, in electrical or signal communication with a controller. The legs are arranged such that they define a common intersection region from which each leg extends. The exemplary embodiment includes a wide array of arrangements and configurations. For example, a multi-leg assembly including four legs can be used in which each leg extends outward from the intersection region at an angle of 90 degrees with respect to an adjacent leg. Alternatively, an assembly can be used in which the legs are arranged such that an angle of less than 90 degrees is defined between two adjacent legs. Or alternatively, the legs may be arranged such that an angle of greater than 90 degrees is defined between two adjacent legs. In certain embodiments, the intersection region may include a collection of point electrodes. Generally, these are individually addressable electrodes and when properly activated by a controller, can induce traveling waves across the intersection region in a variety of fashions. For example, vertical rows of point electrodes can be simultaneously activated to thereby induce traveling waves laterally across the intersection region. In contrast, rows of point electrodes can be activated to induce traveling waves to travel in a transverse direction across the region. Instead, or in addition, the intersection region may also include a collection of concentrically arranged arc electrodes. These can be sequentially activated to cause particulates to be focused to a center point, or alternatively, to spread out as they move radially outward. Each of these multi-leg assemblies is described in greater detail as follows.

Referring to FIG. 1, an exemplary embodiment system 100 is depicted comprising a collection of traveling wave grids. System 100 comprises traveling wave grids or arms, as noted, A-D; and a centrally disposed intersection region 10. A particle stream administered or supplied from the left in the A arm can be further transported to the B arm by driving the vertical columns of electrodes in the cross region 10 in phase and ideally in a sequential fashion, in the direction of A to B. In a related fashion, a layer of particles having been administered or supplied to the intersection region 10 can be transported up to C, down to D, divided so that a portion goes to C and another portion part goes to D, etc. If the phasing of the B array is opposite to that of the cross region 10, particles can be accumulated at the boundary between B and the intersection region 10. Then other particles can be transported into the intersection region 10 from A, C or D, and so provide a form of addition. Mixing can be achieved, for example, by exercising the particles using pseudo-random phases applied to the electrodes within the intersection region 10. The exemplary embodiment includes the use of a collection of individually addressable point electrodes within the intersection region. In the system 100 shown in FIG. 1, the point electrodes can be arranged in a rectangular matrix, however the exemplary embodiment includes a wide array of other arrangements and configurations.

Other systems or structures such as system 100 can be easily and inexpensively fabricated in a multilayer printed circuit board configuration using surface mounted high voltage array drivers, such as those available from SuperTex or the like. Heatable reaction regions can be included in the systems. Particle detection and analysis systems and components can also be integrated to enable property sensitive operations, including but not limited to feedback for determining completion of mixing, reaction, clearing, etc. Multiple layers of particle streams can be transported or otherwise selectively directed by stacking such boards and using vertical traveling wave gates to control inter-board flows. These aspects are described in greater detail herein.

More specifically, the exemplary embodiment relates to aspects in which properties found through spectrographic or other analyses are used to determine or identify classes of particles, and this information enables sorting through the use of one or more traveling wave grids. Referring again to FIG. 1, a sorting function can be performed if one or more positively charged particles are transported along branch A to the right, by continuing the traveling wave along branch C, and applying a positive voltage or reversed phasing to the B branch. As a result, the particles would be driven along branch C. A wide array of transport schemes can be implemented, particularly within the intersection region 10 shown in FIG. 1. For example, particles can be induced to travel in a direction within region 10, from A toward B, and then in a different direction while still within region 10, from D toward C. It is also contemplated that particles can be driven in a direction other than orthogonal directions toward A, B, C, or D. For example, particles could be induced to travel along a diagonal line extending from a location between C and B, to a second location between A and D. It is also contemplated to induce particles to travel along arcuate or curved paths within region 10.

Figure 2:
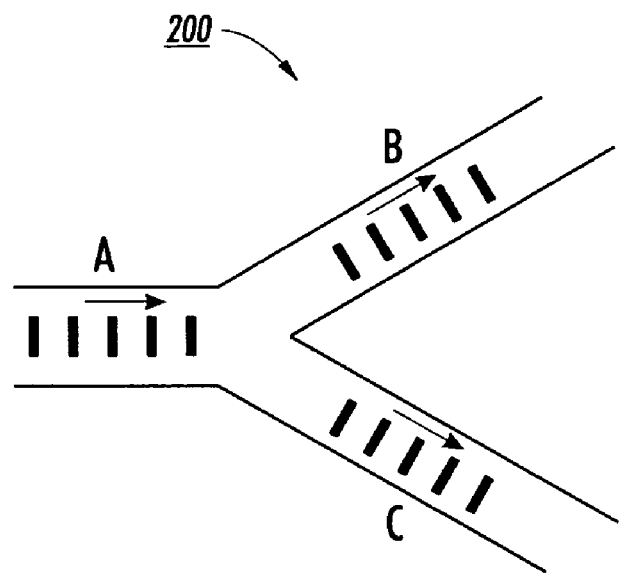
FIG. 2 is a schematic illustration of another exemplary embodiment system for transporting particles.

FIG. 2 depicts a system 200 with diverging (sorting) branches where particles can be driven along either branch B or branch C controlled by information determined along path A, such as for example a spectrographic analysis. Additional or subsequent differential analysis or processing can be done along each branch B and/or branch C.

Figure 3:
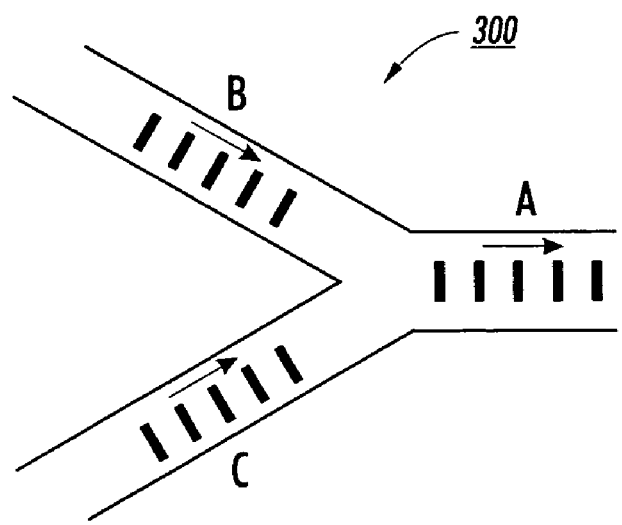
FIG. 3 is a schematic illustration of another exemplary embodiment system for transporting particles.

FIG. 3 illustrates a system 300 with converging (joining) branches where particles coming in along branches B and C can be brought together along branch A to create a mixture that can have appropriate composition or reactions. In FIG. 3, system 300 illustrates converging paths that allow particles to be brought together from different sources, supporting creating mixtures of particles in a controlled way, and supporting chemical and physical interactions between particles.

Figure 4:
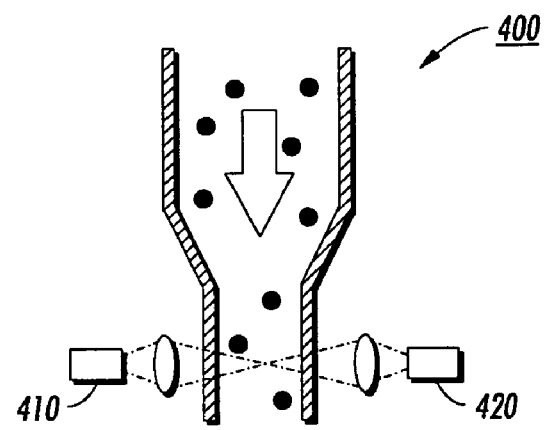
FIG. 4 is a schematic illustration of a conventional system used for transporting particles past an optical spectroscopy system.

Detecting and analyzing particles carried in a fluid stream, such as for example gas or liquid, can be performed in a conventional manner by directing a fluid stream, which is typically in the form of an aerosol, past a focused optical spectroscopy system. FIG. 4 illustrates such a system 400. Particles entrained in an air stream flow past a focused light source 410, such as an LED, and a detection system 420, such as a spectroscopic detection system. The dilute aerosol is inefficiently analyzed because only a few of the particles pass within the focal region of the optical system.

The exemplary embodiment also provides a particle concentrating and collecting component which, for example, is adapted for use in an analytical instrument. The particle concentrating and collecting component includes a member having an inlet and one or more optional outlets, and an interior surface which defines a hollow region for receiving a sample for analysis. The particle collecting component also comprises a traveling wave grid assembly disposed or otherwise positioned along the interior surface of the member. The grid includes a collection of traveling wave electrodes. The traveling wave grid is disposed within the interior surface of the member such that upon operation of the grid, particles in the sample are selectively moved to an analysis region within the instrument. The analysis region can, for example, coincide with the focal region or near-field of the instrument if the instrument is optically based.

The particle concentrating and collecting component may use an electrostatic precipitator to aggregate or otherwise collect or concentrate particles in the sample onto the traveling wave surface when the sample is administered or deposited within the particle collecting component. An electrostatic precipitator is a device which removes particles from a fluid stream. It accomplishes particle separation by the use of an electric field which imparts a positive or negative charge to the particle, attracts the particle to an oppositely charged plate or tube, and removes the particle from the collection surface to a hopper by vibrating or rapping the collection surface. The concentrator is optional; however for most applications it is contemplated to use a concentrator in conjunction with a traveling wave grid. Generally, if a concentrator is used, it is positioned upstream of one or more traveling wave grids in a large volume region of the flowing gas or liquid. If the concentrator is a precipitator, then the precipitator is positioned and operated such that particulates are field ionized and electrostatically drawn to the traveling wave grid. The grid can be used as the collection electrode (negative) by applying a voltage to the electrodes opposite to that of the ionizing electrode (positive). Upon placement within the field of the grid, the particulates can be selectively transported to one or more regions of interest. The concentrator can be in the form of a flow through filter with the traveling wave grid fabricated on the surface of the porous material or on non-porous segments of the filter. This is described in greater detail herein.

Figure 7:
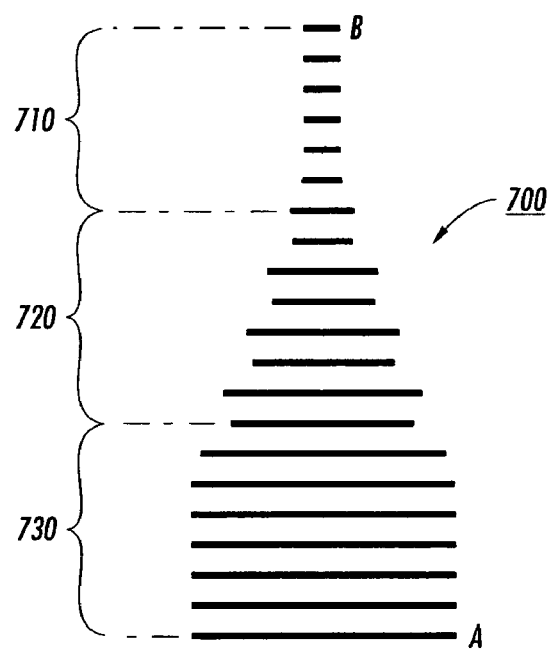
FIG. 7 is a schematic of an exemplary embodiment traveling wave grid configuration.
Figure 8:
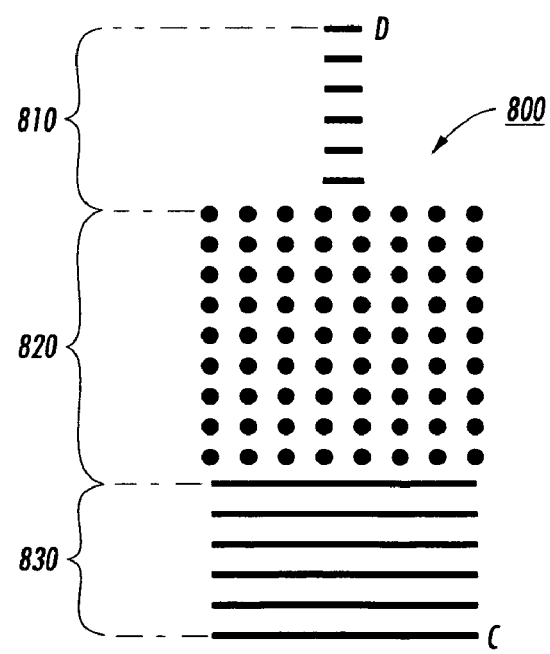
FIG. 8 is a schematic of another exemplary embodiment traveling wave grid configuration.

Specifically, the exemplary embodiment also provides an optical detection system comprising a member having an inlet, an optional outlet, and an interior surface defining a generally hollow interior extending therebetween. The hollow interior is adapted for receiving a sample for analysis or detection by the instrument. The optical detection system also includes a light generating component disposed in the member which is in communication with the hollow interior. The optical detection system further includes a light detector disposed within the member and in communication with the hollow interior of the member. The light detector is adapted to detect light within the hollow interior. The optical detection system also includes a traveling wave grid disposed along at least a portion of the interior surface of the member. The traveling wave grid is adapted to transport sample to the region between the light generating component and the detector. The optical detection system may use a traveling wave grid which is optically transparent or substantially so. Alternatively, the near field or focus waist of the optical fields can have a width less than the gap width between traveling wave electrodes. In certain versions, the optical detection system may use a light generating component which is in the form of a light emitting diode. Similarly, the light detector may be in the form of a spectroscopic detector. Moreover, the optical detection system may additionally utilize an optics system positioned between the light generating component and the light detector. The optics system focuses light emitted from the light generating component within a focal region of the light detector. Additionally, the optical detection system may utilize a hollow interior which varies in cross sectional region to further promote concentration of particulates or of the sample. For example, the hollow interior may include a first region near the inlet and a second region near the light detector. The second region has a cross sectional area that is less than the average cross-sectional area of the first region. Alternatively, as described below, the interior has a constant cross-sectional area but the traveling wave electrodes converge as shown in FIGS. 7 & 8. A wide array of optical detection devices can be used in conjunction with the traveling wave grids described herein. For example, in addition or instead of those noted herein, light scattering angular detectors, which are not necessarily spectroscopic in nature, can be utilized.

Figure 5:
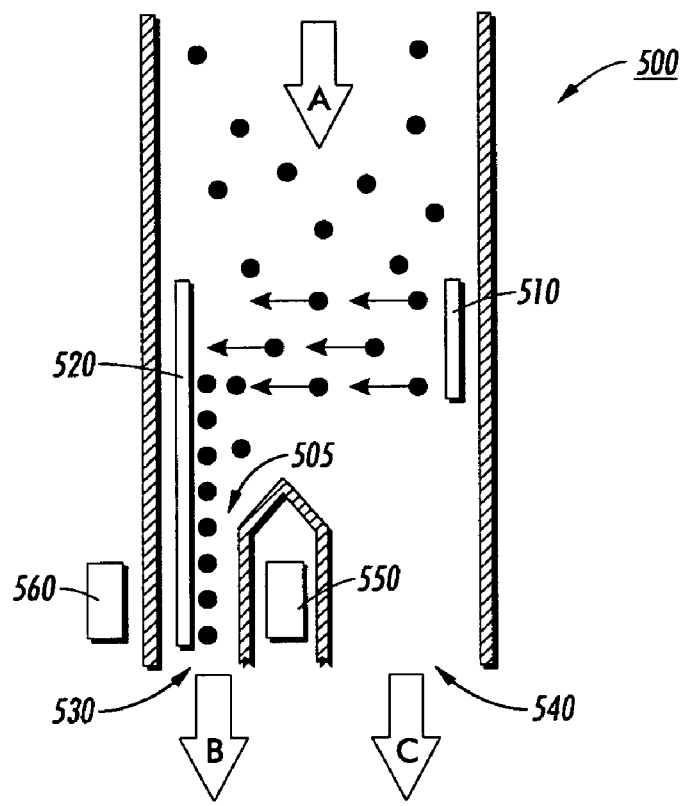
FIG. 5 is a schematic illustration of an exemplary embodiment system used for transporting particles past an instrumentation system.

The present exemplary embodiment provides a strategy and system to concentrate and transport particles as well as a near field detection system enabled by the transport system. As shown in FIG. 5, a system 500 is provided that utilizes an electrostatic precipitator 510 or other concentration system or component to aggregate the particles suspended in an insulating fluid, such as for example air, deionized water, or oil onto a surface. The surface supports an electrostatic traveling wave grid 520. These components can be located within a narrowed region 505. The collected charged particles are translated along the surface by the phased fields on the electrodes of the grid 520. The substrate of the traveling wave grid 520 is transparent so that, when the particles pass between electrodes, an optical system 550, 560 can detect them. The electrodes themselves could be transparent, such as if formed from indium tin oxide (ITO). Specifically, the system 500 can utilize an output or branch such as 530 for discharging particles residing or transported by the grid 520. The system 500 can also utilize an output 540 for discharging medium from which the particles have been removed. In operation, a flowing medium containing sample such as particles, shown as arrow A, is directed to the narrowed region 505 at which particles are collected on the traveling wave grid 520. Such collection can be significantly enhanced by the use of the precipitator 510. A discharge containing a relatively high concentration of particles, such as shown by arrow B, can be directed through the branch 530 to one or more further detection or analytical devices. The output 540 directs medium from which particles were removed, shown as arrow C, to a reservoir, final filter, drain, or the like.

Figure 6:
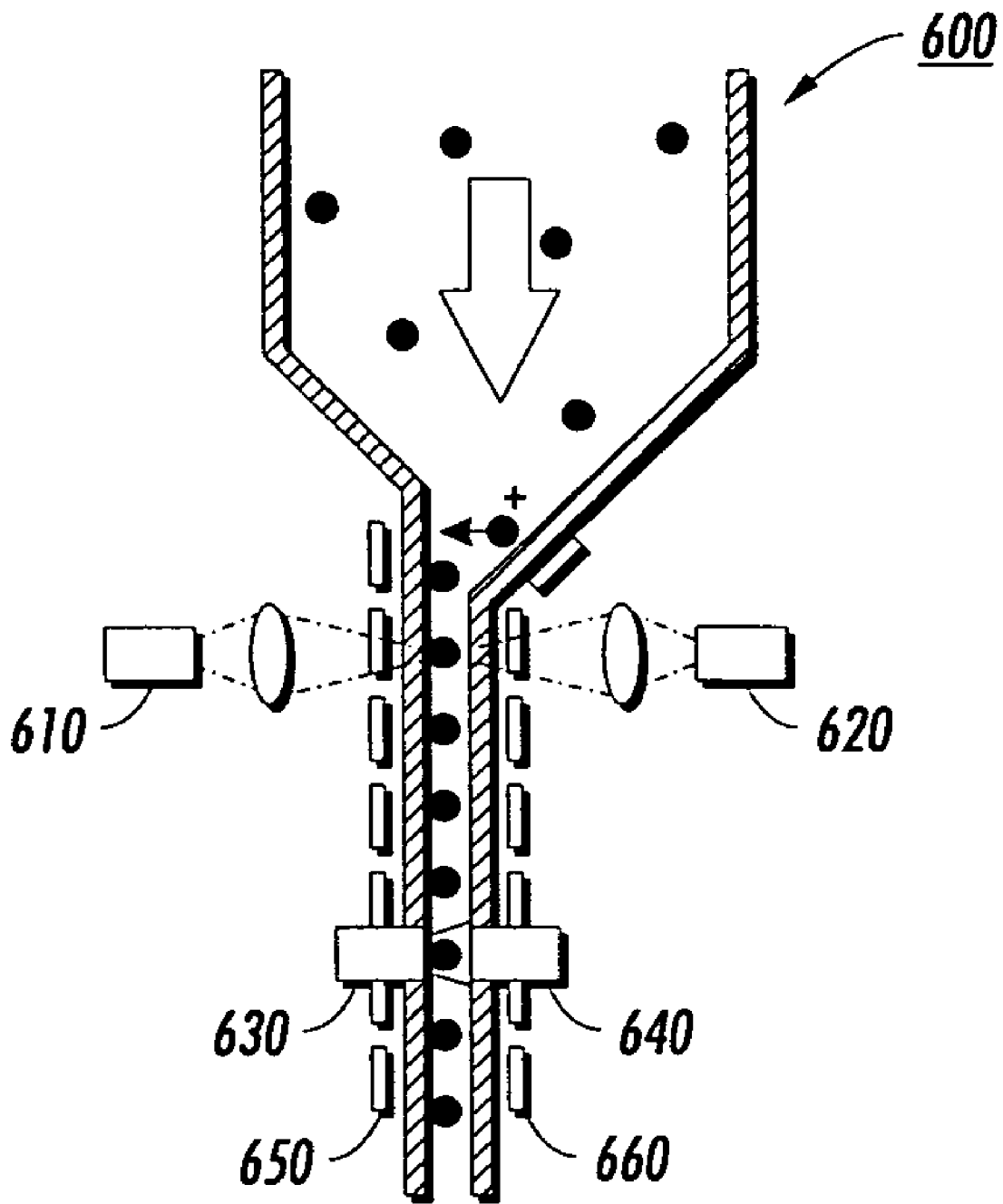
FIG. 6 is a schematic illustration of an exemplary embodiment system used for transporting particles past one or more optical detection systems.

FIG. 6 illustrates another exemplary embodiment system 600 including two types of optical detection systems. The first type or version utilizes optics to focus the light for irradiation and detection. Specifically, a light source 610 emits light that is absorbed and re-emitted at lower energies by the particles. The emitted light is spectroscopically sensed by a detector 620, such as a spectroscopic detector whereas light at the energy of the light source 610 is blocked from the detector 620 by an optical filter. An advantage of the strategy of configuration 600 is that the particles, and generally all particles, are confined to a space within the focal region of the optics, for example 610, 620, so much higher and complete detection can be performed. The second sensing system includes a light source 630, such as an LED, and a detector 640, such as a spectroscopic detector. A collection of traveling wave grids 650, 660 are provided within or generally along the region of analysis of the system 600. The second sensing system eliminates or avoids much of the optics and generally increases the system efficiency by illuminating and collecting the light in the near field. This allows less power to be used and less expensive and more compact systems to be designed. It will be appreciated that the exemplary embodiments include the use of only one, two, or three or more separate traveling wave grids disposed anywhere along a collecting or analysis region of an instrument.

Referring to FIGS. 7 and 8, various configurations are illustrated for traveling wave grids used in the systems and applications described herein. FIG. 7 depicts a traveling wave grid 700 having a tapering configuration and including at least a narrow region 710, an expanded region 730, and an intermediate region 720. In the event that particles are induced to travel from position B to position A on the grid 700, a dilution effect can be achieved. In contrast, if particles are induced to travel from position A to B on the grid 700, a concentrating effect can be achieved. The grid 700 can include other regions in addition to, or instead of, regions 710, 720, and 730. FIG. 8 illustrates a traveling wave grid 800 having a stepped configuration and including at least a narrow region 810, a selectively controllable region 820, and an expanded region 830. The region 820 includes a collection of point electrodes which may be operated to induce particular desired patterns or configurations of traveling waves or wave packets. It will be appreciated that traveling waves can be induced upon the grid 800 to cause particles to travel from position C to D, or D to C, or any other path desired. The grid 800 can include other regions of traveling wave electrodes in addition to, or instead of, those shown in FIG. 8. Although the grids 700 and 800 are shown as generally two dimensional, the exemplary embodiments include the use of three dimensional grid configurations.

Figure 9:
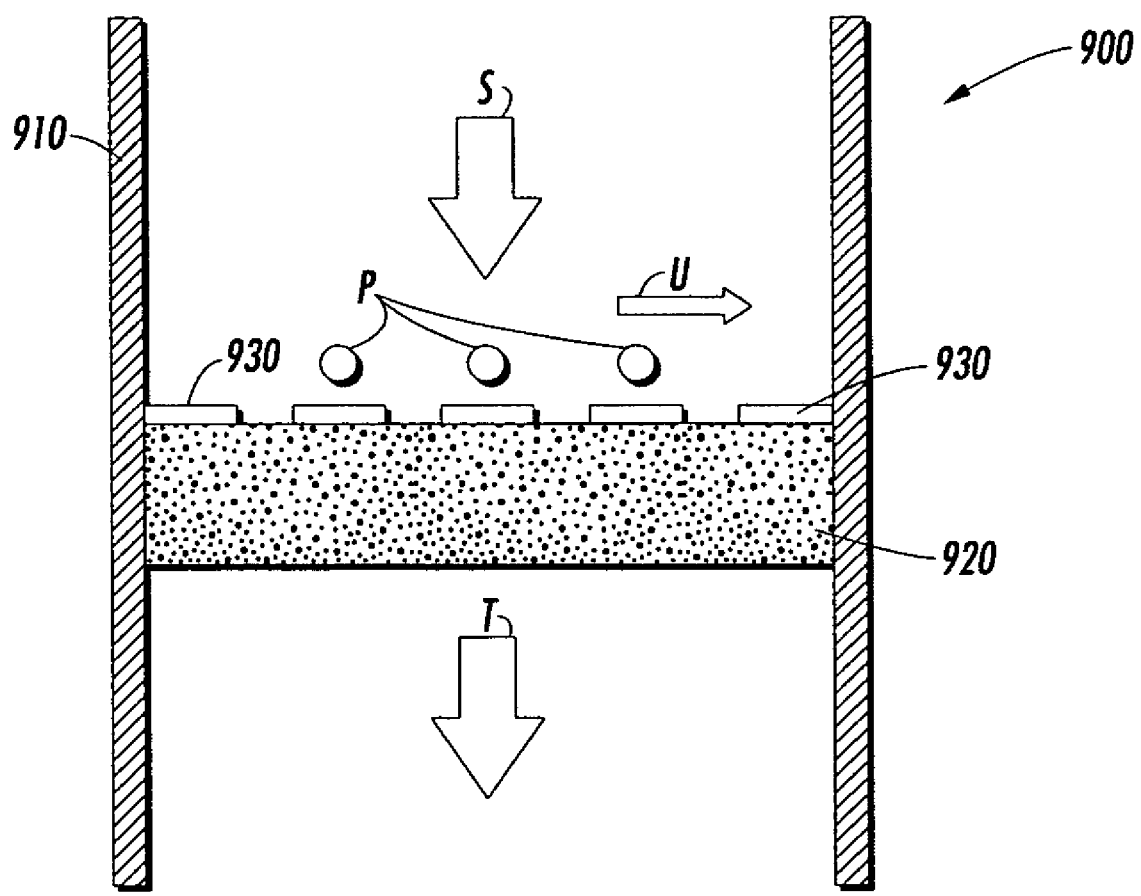
FIG. 9 is a schematic of an alternate embodiment concentrator.

FIG. 9 is a schematic of another exemplary embodiment concentrator system 900. System 900 can be located or positioned within a flow channel, such as defined by 910, through which a flow stream S travels. The flow stream S contains particles P dispersed throughout. The system 900 includes a filter body 920 that filters particles P from the flow to result in a discharge stream T. The filter body 920 can extend at least partially across, or entirely across, the region defined by the member 910 for the flow stream. The filter body 920 can be relatively uniform and be comprised of a porous material known in the art which is useful for filtering operations. Alternatively, the filter body 920 can define regions of non-porosity. Provided along the exposed face of the filter body 920 facing flow stream S, is a traveling wave grid 930. The grid 930 can be operated to transport particles P from one region of the face to another region, such as in the direction of arrow U. As will be appreciated, a particle receiving port (not shown) can be provided in the flow channel 910 or the filter body 920 to receive particles P after having been collected or concentrated by the filter body 920 and the traveling wave grid 930.

Generally, upon incorporation of a traveling wave grid in an instrument using a concentrator, operation is as follows. After concentration onto the plane of the traveling wave grid, the grid can focus and thus further concentrate the particulate stream before presentation to an optical system or other analytical device using a converging pattern (either linear or curvilinear) in the electrodes or using a two dimensional array. The system can also be utilized without the use of an electrostatic precipitator or in-wall filter. The walls (or traveling wave grids) along which the sample stream containing particulates pass, can be curved, flexible, or conformal.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A system for collecting particles and transporting the collected particles, the system comprising:
    a source of sample dispersed in a gas or liquid medium;
    a concentrator in communication with the source and adapted to collect the sample, wherein the concentrator is an electrostatic precipitator;
    a traveling wave grid extending from a first location at which the concentrator is located, to a second location;
    wherein upon operation of the concentrator and the traveling wave grid, sample is collected from the medium and transported to the second location.

2. The system of claim 1 wherein the sample includes particulates dispersed in a gas or liquid medium.

3. The system of claim 1 wherein the sample includes liquid droplets dispersed in a gaseous medium.

4. The system of claim 1 further comprising:
    a device disposed at the second location, the device adapted to perform a detection and/or analytical operation.

5. The system of claim 4 wherein the device includes a light generating component and a light detector spaced from the light generating component whereby upon operation of the device, the collected sample passes between the light generating component and the light detector.

6. The system of claim 5 wherein the light generating component is a light emitting diode and the light detector is a spectroscopic detector.

7. A system for collecting particles from a medium and subjecting the collected particles to an analytical operation, the system comprising:

a source of sample dispersed in a medium;

a concentrator in communication with the source of the sample, the concentrator including an electrostatic precipitator;

a device adapted to perform a detection and/or analytical operation; and a traveling wave grid extending between the concentrator and the device and adapted to transport collected sample to the device.

8. The system of claim 7 wherein the sample includes particulates dispersed in a gas or liquid medium.

9. The system of claim 7 wherein the sample includes liquid droplets dispersed in a gaseous medium.

10. The system of claim 7 wherein the device is an optical detection device.

11. The system of claim 10 wherein the device includes a light generating component and a light detector spaced from the light generating component whereby upon operation of the device, the collected sample passes between the light generating component and the light detector.

12. The system of claim 11 wherein the light generating component is a light emitting diode and the light detector is a spectroscopic detector.

13. The optical detection system of claim 11 further comprising:

an optics system disposed between the light generating component and the light detector, the optics system adapted to focus light emitted from the light generating component within a focal region of the light detector and containing the transported sample.

14. The optical detection system of claim 11 wherein the light generating component is positioned in the device such that collected sample passes through the near field of the light generating component.

15. The optical detection system of claim 13 wherein the light detector is a spectroscopic detector.

16. The system of claim 7 wherein the traveling wave grid is optically transparent.

* * * * *